United States Patent [19]

Kihira et al.

[11] Patent Number: 4,806,849
[45] Date of Patent: Feb. 21, 1989

[54] METHOD AND APPARATUS FOR DIAGNOSING DEGRADATION OF COATING FILM ON METAL MATERIAL

[75] Inventors: Hiroshi Kihira; Satoshi Ito; Tomomi Murata, all of Kawasaki; Shunji Sakamoto, Kitakyushu; Kazuo Yamamoto, Tokyo, all of Japan

[73] Assignee: Nippon Steel Corporation, Tokyo, Japan

[21] Appl. No.: 30,515

[22] Filed: Mar. 27, 1987

[30] Foreign Application Priority Data

Mar. 31, 1986 [JP] Japan .................................. 61-73758

[51] Int. Cl.$^4$ .................... G01N 27/26; G01R 27/02
[52] U.S. Cl. ............................... 324/65 CR; 204/404; 427/10
[58] Field of Search ................. 324/65 CR, 65 R, 62, 324/71.2, 71.1, 72.5; 204/1 T, 404; 427/8–10

[56] References Cited

U.S. PATENT DOCUMENTS

| | | | |
|---|---|---|---|
| 3,967,197 | 6/1976 | Anderson | 324/61 R |
| 4,197,176 | 4/1980 | Ensanian | 324/71.1 X |
| 4,221,651 | 9/1980 | Mansfeld | 204/404 X |
| 4,238,298 | 12/1980 | Tsuru et al. | 204/404 X |

FOREIGN PATENT DOCUMENTS

5477191 12/1977 Japan .

OTHER PUBLICATIONS

Ito et al., A New Method to in situ Monitor Corrosion Protectivity of Rust on Weathering Steel, 5-1986.
Denki Kagaku (Electro Chemistry) No. 23, 1955, pp. 15–18.
Kogyo Kagaku (Industrial Chemistry), vol. 61, No. 3, 1958 pp. 291–295.
Collection of Lectures on the 30th Anti-Corrosion Symposium B-212, 1983.
Bosyoku Gijutsu, (Corrosion Protecting Technology), vol. 34, No. 8, 1985, pp . 464–465.

*Primary Examiner*—Reinhard J. Eisenzopf
*Assistant Examiner*—Jack B. Harvey
*Attorney, Agent, or Firm*—Pollock, Vande Sande & Priddy

[57] ABSTRACT

Method and apparatus for diagnosing degree of degradation of a coating film of a painted metal material by dividing the surface of the painted metal material into a number of small area zones, measuring impedance of the coating film at each of the zones through an AC impedance measuring technique, determining a statistic distribution and/or a two-dimensional distribution of impedance values measured at the individual zones to thereby determine the degree of degradation of the coating film of the painted metal material on the basis of the aforementioned distribution(s).

8 Claims, 8 Drawing Sheets

7 PORTIONS OF RELATIVELY LOW IMPEDANCE

METHOD AND APPARATUS FOR DIAGNOSING DEGRADATION OF COATING FILM ON METAL MATERIAL

BACKGROUND OF THE INVENTION

The present invention relates to a method of measuring the degree of degradation of a coating film on a painted material and an apparatus for carrying out the same. More particularly, the invention is concerned with a method of measuring quantitatively the corrosion preventing capability of a coating film of a painted steel material and an apparatus for carrying out the method.

Metal, material such as steel, is usually in use with a paint film coated thereon for protecting the metal material against corrosion. The coating film is degraded or deteriorated in the course of time lapse under the influence of ultraviolet rays, moisture, corrosion of substrate metal and other factors. For determining the time for recoating (repainting) as well as for the maintenance of large scale steel structures, such as bridges, buildings, factory equipment and the like and transportation vehicles or tools, such as automobiles, ships, containers and others, it is extremely important to quantitatively measure the corrosion preventing function or capability of the coating films (paint films) to thereby determine accurately and objectively the degree of deterioration thereof.

As the methods of measuring nondestructively the degree of deterioration of the films coated on the metal material, there have heretofore been know a method of measuring change in brilliance and color, a method of measuring an insulation resistance and a method of measuring AC impedance.

In conjunction with the AC impedance measuring method, it is known to measure parallel resistance and parallel capacity which balance with a system to be measured, by using AC currents of frequencies varying over a wide range, to thereby establish the relationships between the measured values and the frequencies, or determine the phase differences tan δ on the basis of the parallel resistance and the parallel capacity to thereby establish the relationships between the phase difference tan δ and the frequencies. These relations are then utilized for determining the corrosion preventing effect (as known, for example, from a Japanese periodical "Denki Kagaku or Electrochemistry in English", No. 23, 1955, pp. 15 to 18, and a Japanese periodical "Kogyo Kagaku Zasshi or Industrial Chemistry Magazine", Vol. 61, No. 3, 1958, pp. 291–295) or to measure the impedances and the phase differences over a wide frequency range covering a high frequency (10 KHz to 100 KHz) to a low frequency (1 mHz to 100 mHz) [as known, for example, from "Collection of Lectures on the 30-th Anti-Corrosion Symposium", B-212 (1983)].

These methods are adopted mainly at the level of laboratories for analyzing a sample piece for test or monitoring a test piece mounted on an actual structure. However, these methods can not be employed for evaluating the corrosion preventing capability of a coating film at arbitrary points of the actual structure because of restriction imposed on the apparatus for carrying out the method.

On the other hand, there is known a method of evaluating the corrosion preventing capability of a coating film at arbitrarily selected locations of an actual structure in accordance with the AC impedance measuring principle. According to this method, electrodes are disposed at a substrate metal material and a surface of a coating film for constituting a balanced detection circuit by inserting a filter sheet impregnated with liquid electrolyte between the electrodes to thereby measure the impedance (as known, for example, from Japanese Patent Laid-Open Application No. JP-A-54-77191, published June 20, 1979).

This method is based on the prerequisite that the coating film is uniform over the area where measurement is performed in order to obtain the characteristic value of that area through a single-point measurement. However, the coating film actually applied is inherently nonuniform in respect to the film thickness and other factors, and the degradation of the coating film progresses in such a manner as to promote the nonuniformity more seriously. This fact is not taken into consideration by the method mentioned above.

When a coating film undergone degradation to a certain extent is carefully observed, it is commonly found that the coating film is locally delaminated, rust is produced in a spot-like pattern, a small bulge is formed and/or that the film is partially chalked. Thus, it is naturally difficult to determine accurately and quantitatively the state of a coating film undergone nonuniform degradation as mentioned above through the conventional single-point AC impedance measurement.

Thus, there exists a demand for a method and an apparatus which is capable of accurately and quantitatively determining the degraded state of a coating film which tends to undergo nonuniform degradation and diagnosing quantitatively the degree or extent of degradation of a coating film applied onto a metal material, for ensuring effective operation and utilization, i.e., maintenance, updating measures, and lengthened use life of public and private facilities such as large scale steel buildings, transportation tools and the like.

SUMMARY OF THE INVENTION

It is an object of the present invention to provide a method of diagnosing quantitatively the degree or extent of degradation of a coating film applied on a metal material by dividing a painted surface of the metal material to be measured into a number of small area zones and measuring impedances of the coating film at the painted metal surface zones by an AC impedance measurement technique to thereby determine quantitatively the degradation of the coating film on the basis of the measured impedance values taken at the number of coating film zones as well as an apparatus for carrying out the method.

According to the invention, the surface of a painted metal material to be measured is divided into a number of small areas or zones, wherein impedance of the coating film is measured for each of the small zones through the AC impedance measurement technique, the impedance values of the coating film zones resulting from the measurement being processed statistically to thereby determine the degree of degradation of the coating film.

According to one embodiment of the present invention, there is provided an apparatus for carrying out the method of determining diagnostically the degree of degradation of the coating film with high efficiency, which comprises a grid-like jig for dividing the surface of a painted metal material to be measured into a plurality of small area zones, AC impedance measuring means, and a detector for measuring impedance of the coating film at the small area zones in cooperation with the AC impedance measuring means. The detector has an open mouth portion of such size and shape which allow the detector to be brought into close contact with the coated metal surface at each of the small area zones and an electrolyte holding chamber communicated with the open mouth portion and having an electrode for electrolysis mounted internally of the chamber, which holds a liquid electrolyte therein.

Further, according to another embodiment of the present invention, there is provided an apparatus for determining diagnostically the degree of degradation of a coating film of a painted metal material, which comprises AC impedance measuring means, a plurality of detectors, each suitable for measuring the film impedance at a small area zone of the coated surface of the metal material to be measured in cooperation with the AC impedance measuring means and including an open mouth portion capable of contacting closely with the surface of the painted metal material at the small area zone and an electrolyte holding chamber communicating with the open mouth portion and holding internally an electrode for electrolysis and a liquid electrolyte. A multiplexer is connected between the plurality of the detectors and the AC impedance measuring means for supplying output signals of the plurality of detectors to the AC impedance measuring means.

In conjunction with the terminology used in the specification, it is to be understood that "measurement of the coating film impedance through AC impedance technique" or similar expression is intended to mean a method of measuring impedance of a coating film by disposing an electrode for electrolysis in opposition to a metal substrate for the coating film to be diagnosed which substrate serves as the other electrode for electrolysis and forming a small cell by feeding a liquid electrolyte between both electrodes, wherein a voltage response produced upon application of an AC current to the cell is utilized for determining the impedance.

DESCRIPTION OF THE PREFERRED EMBODIMENTS

Figure 1:
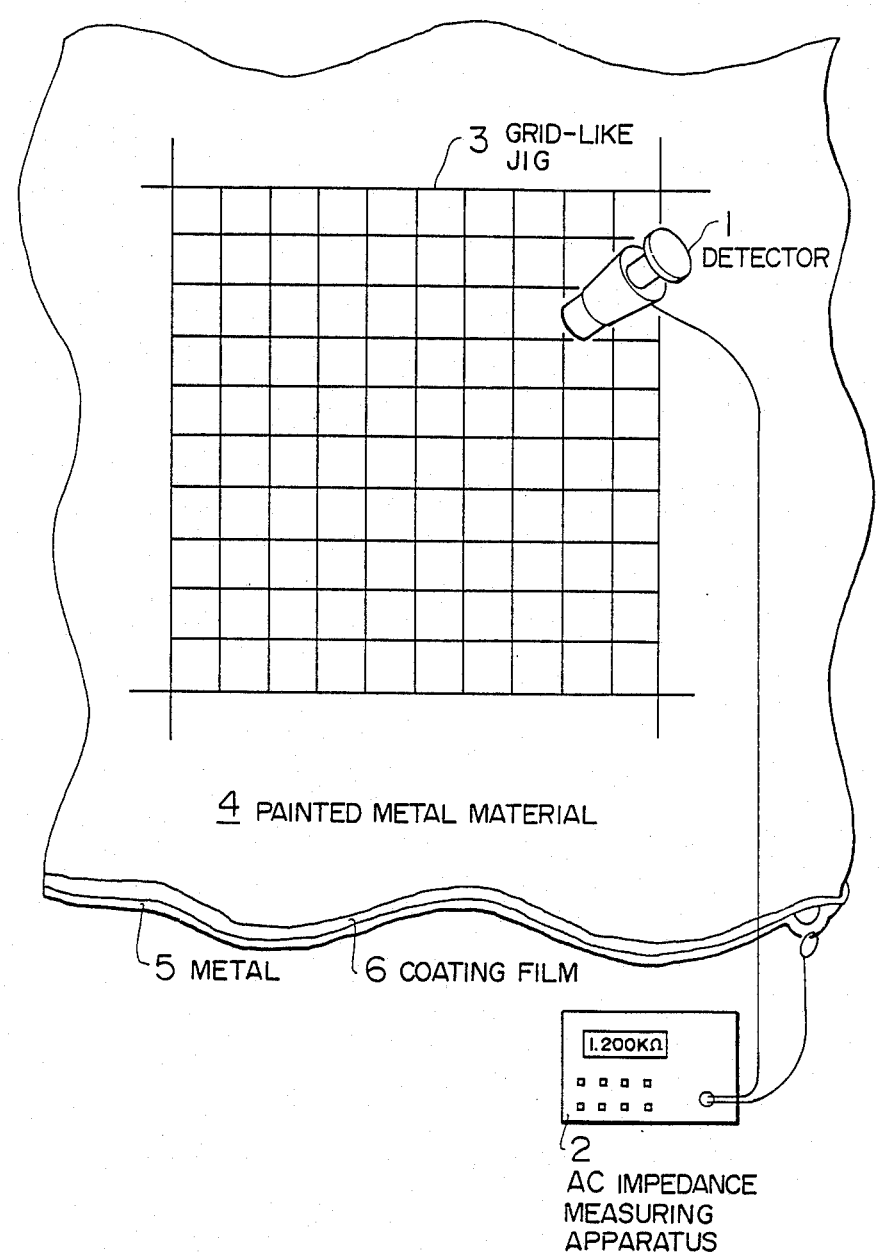
FIG. 1 is a view showing schematically an arrangement of a diagnosis apparatus according to an exemplary embodiment of the present invention.

The basic principle underlying the present invention will be described by referring to FIG. 1.

A grid-like jig 3 is placed on a painted metal material 4 subjected to measurement, and impedance of the coating film is measured through multi-point measurement at zones of the coating film divided by the grid-like jig 3 by means of an AC impedance measuring apparatus 2 and a detector 1. The AC impedance measuring means may be constituted by any one of the apparatus disclosed in a Japanese periodical "Bosyoku Gijutsu (Corrosion Protecting Technology in English)", Vol 34, No. 8, (1985), pp. 464 to 465, "A new method to in situmonitor corrosion protectivity of rust on weathering steel" by S. Itoh et al, presented at "ASTM symposium on degradation of metals in the atmosphere", 12–13, May, 1986, Philadelphia, and Japanese Patent Application Laid-Open No. 77197/1979 (JP-A-54-77191).

For maintaining an acceptable accuracy, the multi-point measurement will require the measuring points in a number at least on the order of 20, and in order to evaluate the coating film in terms of a plane, the number of points at which the measurement is made should preferably be of about 100. The results of the multi-point measurement are rearranged in terms of such statistic distributions as illustrated in FIGS. 2A to 2C for diagnostic judgment.

Figure 2A:
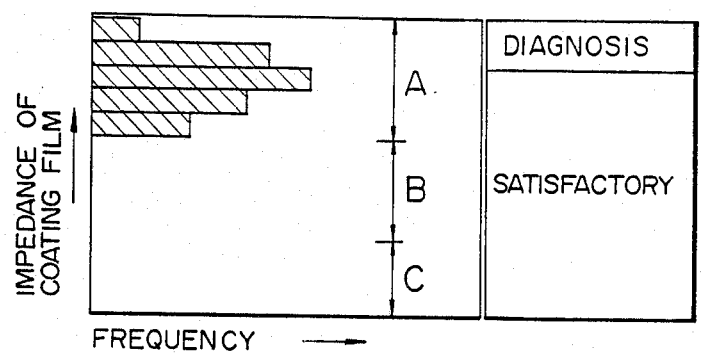
FIGS. 2A, 2B and 2C are views for illustrating statistical distributions of the results of multi-point measurement.
Figure 2B:
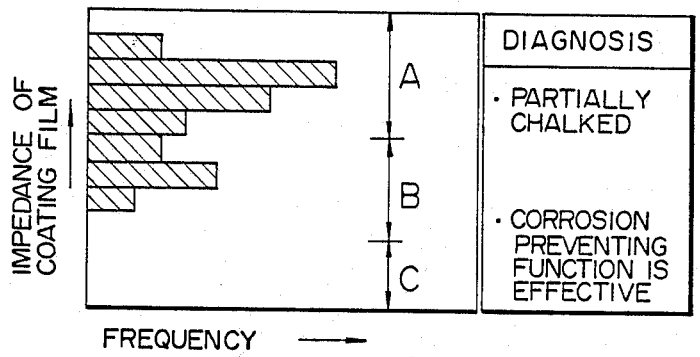
Figure 2C:
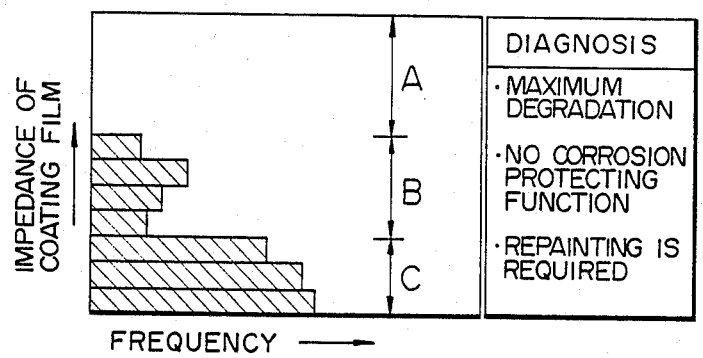

Assuming now that high impedance of a coating film represents the satisfactory state with low impedance representing the degraded state, the results of measurement can be classified into ranges A, B and C as shown in FIGS. 2A, 2B and 2C. More specifically, in the impedance range A, the coating film as measured is regarded to be satisfactory. In the impedance range B, the coating film is degraded but has a corrosion protecting capability. In the impedance range C, the coating film is considered as having no corrosion protecting capability and suffering delamination of the coating film and formation of rust.

On the assumption described above, it is possible to diagnose quantitatively the degree of degradation of the coating film by observing the statistic distribution of the film impedance values.

It should be mentioned here that the division of the surface of a painted metal material subjected to the measurement into a number of small areas or zones at a predetermined interval is not restricted to the use of the illustrated grid-like jig but other various division schemes may be adopted in dependence on the objects to be measured. By way of example, the measuring points may be identified by marking by a stamp, a writing pen or other.

As to the function of the detector, it is only required that the AC impedance measurement can be conducted by using a liquid electrolyte. To this end, the detector may include at least an electrolyte holding chamber having an open mouth portion brought into contact with the object to be measured and an electrode for electrolysis, wherein the electrolyte holding chamber may be constituted by a mass of sponge or a container of a small volume, while the electrode may be made of an insoluble electrode material such as platinum.

Figure 3:
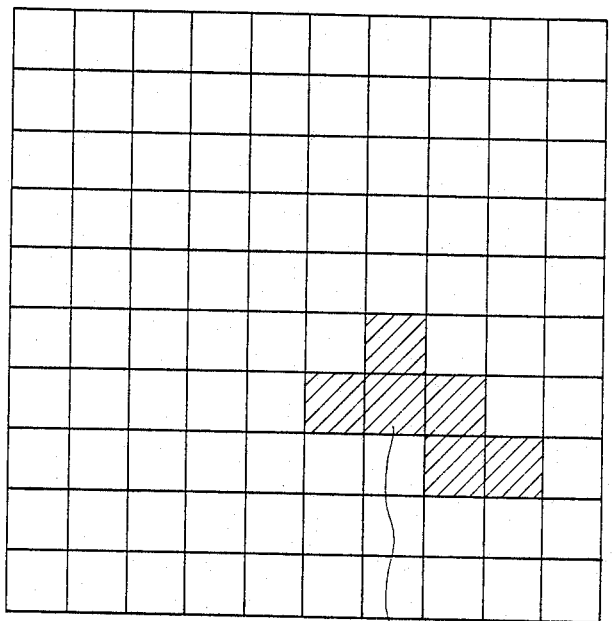
FIG. 3 is a view showing a two-dimensional distribution of the results of the multi-point measurement.

FIG. 3 illustrates a method of rearranging the results of the multi-point measurement in the form of two-dimensional distribution. The multi-point measurement was performed on a substantially satisfactory coating film belonging to the range A by using a grid-like jig. In FIG. 3, the designated points at which the measurements were performed, are shown as they are, while those regions 7 of the coating film which have relatively low impedance are indicated by hatching.

By rearranging the result of measurement in the form of two-dimensional distribution, it can be clearly seen where and at what rate the coating film begins to be degraded. Similar advantage can be obtained by drawing contour lines on the basis of the results of measurement.

Figure 4:
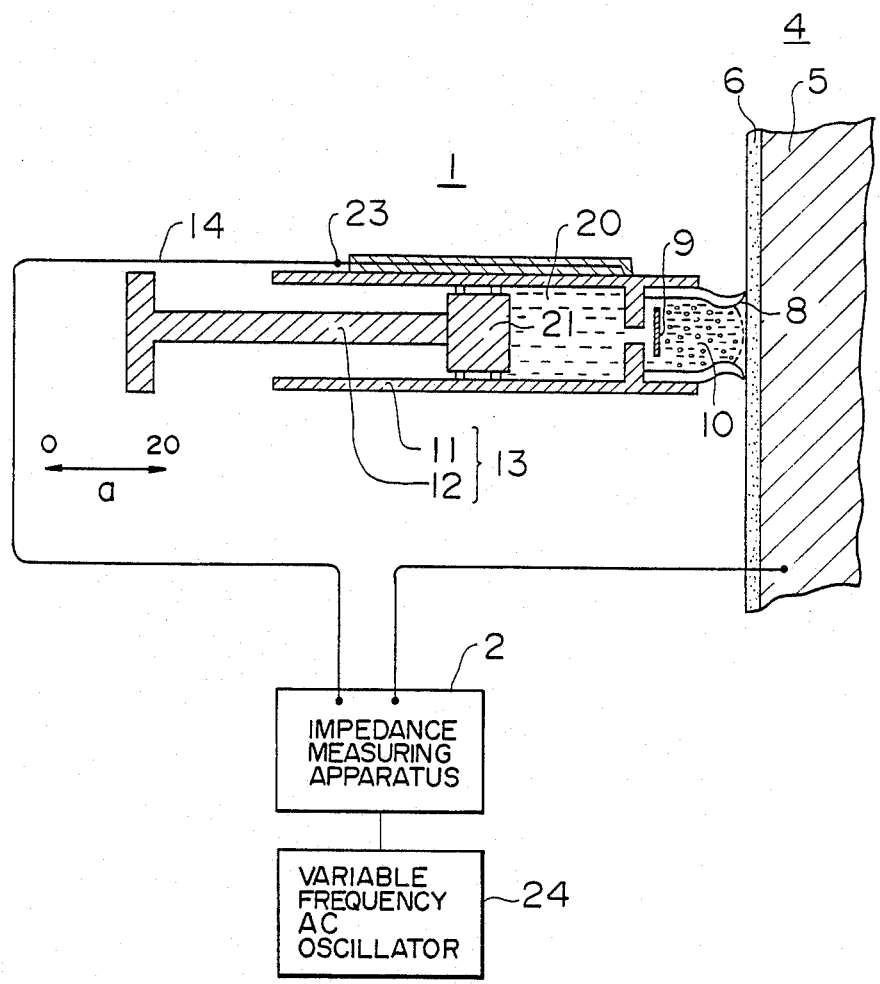
FIG. 4 is a sectional view showing a structure of a detector and its connection to a measuring apparatus.

FIG. 4 shows a structure of the detector. As will be seen, the detector 1 is basically composed of an open mouth portion 8 made of silicone rubber and having an area of 1.2 cm$^2$ (adapted to contact with the coating film 6 of the coated metal material 4 to be measured), an electrode 9 for electrolysis made of platinum or the like, and a liquid electrolyte chamber 10 including a mass of sponge material for facilitating accommodation of the liquid electrolyte. The basic structure of the detector is provided with a liquid electrolyte supplementing apparatus 13 composed of a cylinder 11 made of an insulating plastic material such as acrylic resin and a piston 12, wherein a chamber defined between the cylinder 11 and the piston head 21 is filled with the liquid electrolyte which can thus be injected in the holding chamber 10 by pushing the piston. Further, a reference numeral 23 denotes an output terminal electrically connected to the electrode 9 for electrolysis, and 14 denotes lead wires for electrically connecting the output terminal 23 and the impedance measuring apparatus 2 to each other. The other terminal of the impedance measuring apparatus 2 is electrically connected to the metal substrate 5 of the painted metal. The impedance measuring apparatus receives an AC power from a variable frequency AC oscillator 24. In measurement of the impedance of coating film, the detector 1 is pushed against the coated metal material 4 with the open mouth portion 8 being closely attached to the surface of the material 4 and an AC voltage of controlled frequency is applied to the electrode, while an electrolyte is filled into the chamber 10, so as to cause a small AC current to flow between the electrode 9 and the metal substrate 5. The impedance of the coating film is determined from the impedance value measured under the above condition.

In FIG. 3, a scale a equal to 20 mm is shown for indicating the size or dimensions of the detector manufactured in reality. It should however be understood that the detector may be so configured as to be capable of measuring narrowed or limited portions by decreasing the dimensions of the detector, and/or imparting curved profile. Alternatively, the dimensions or size of the detector may be increased. Further, the liquid electrolyte supplementing apparatus may be of a plunger-like structure or may use a pump.

Figure 5:
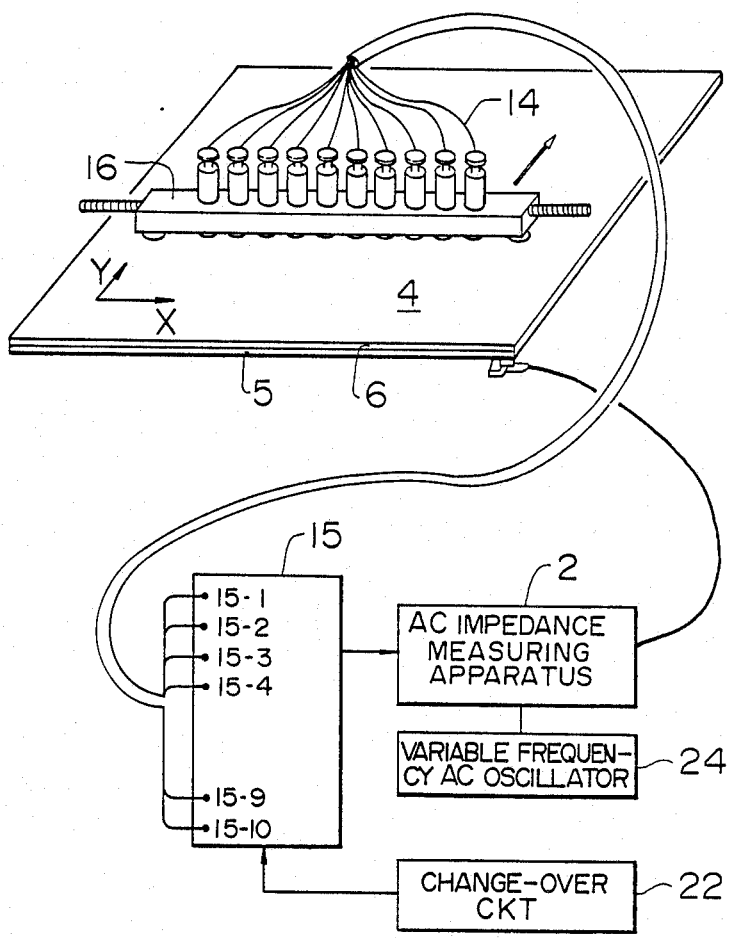
FIG. 5 is a view showing schematically an arrangement of the diagnosis apparatus according to another embodiment of the invention.

FIG. 5 shows an apparatus for diagnosing the degradation of a coating film of a painted metal material according to another embodiment of the invention which is designed to measure the impedance of the coating film at a plurality of points simultaneously at one time.

Next, typical practical applications of the present invention will be described on the assumption that the invention is applied to oil paint/red lead paint/steel substrate combinations, being understood that the invention can also be applied to other paint/substrate combinations through accumulation of available data.

Degradation of a paint film applied to a door made of steel was quantitatively measured by the method according to the invention. The door subjected to the measurement is a part of a building located in a semi-industrial area and remains painted once 22 years ago without being recoated. Specification was such that a red lead paint was used for the ground coating and a gray oil paint was used for a top coating (over coating). The initial film thickness is unknown.

One surface of the door (referred to door outer face) in concern faces exteriorly to the south and suffers chalking and exposure of the ground paint due to the effect of ultraviolet rays, and delamination of the paint film as well as rust are observed here and there.

On the other hand, the opposite face of the door faces interiorly of the building (referred to as door interior face) is quite satisfactory in appearance because it is difficult to be affected by ultraviolet rays and corrosion. A multi-point impedance measurement was carried out by using the detector of the structure shown in FIG. 4 which was filled with an aqueous solution of 0.1 mole sodium sulfate (an electrolyte difficult to change the paint film) at zones divided by a grid-like jig of (10×10)-zone array with pitch of 2 cm.

TABLE 1

| Resistance of Paint film | Optimal Frequency |
|---|---|
| 0–20 Ω | 1.7 kHz |
| 20–200 Ω | 850 Hz |
| 200 Ω–2 kΩ | 450 Hz |
| 2 kΩ–20 kΩ | 250 Hz |
| 20 kΩ–2 MΩ | 100 Hz |
| 2 MΩ–200 MΩ | 500 Hz |

In the AC impedance measurement, an impedance indicative of the ion transmission resistance of the coating or paint film (representing the paint film function of isolating the steel substrate from the environment and referred to as "paint film resistance") has been especially measured. The frequencies at which the paint film resistance can be determined with high accuracy are listed in the table 1.

For determining the degree of degradation of the paint film, it is desirable to measure the ion transmission resistance thereof. In this connection, it should be noted, that the paint film impedance measured by the impedance measuring method includes various parameters in addition to the ion transmission resistance. For example, there exist error due to stray capacitance of a cable interconnecting the impedance measuring apparatus and the detector, error due to electric capacitance of the paint film itself (the error produced at an excessively high frequency and involving the measurement value smaller than the true value), polarization resistance present at the interface between the metal and the paint film, error due to capacitance of corrosion layer (the error produced at an excessively low frequency and resulting in the measurement value larger than the true value) and others. The frequencies listed in the table 1 were selected in dependence on the resistances of the paint film so that the errors mentioned above can be suppressed to minimum.

Under the circumstance, it is expected, that the relations listed in the table may vary in dependence on the painting specification. Thus, selection of the frequencies will have to be made carefully.

In the measurement, pulses of a constant current in a range of 0.01 μA to 10 mA were applied and the range of measurement, as well as frequency were adjusted so that the voltage change, i.e. the voltage response, was lower than 200 mV. The electric connection to the substrate metal of the door subjected to measurement was made to a handle made of a steel alloy electrically connected to the substrate by using a clamping clip.

Figure 6:
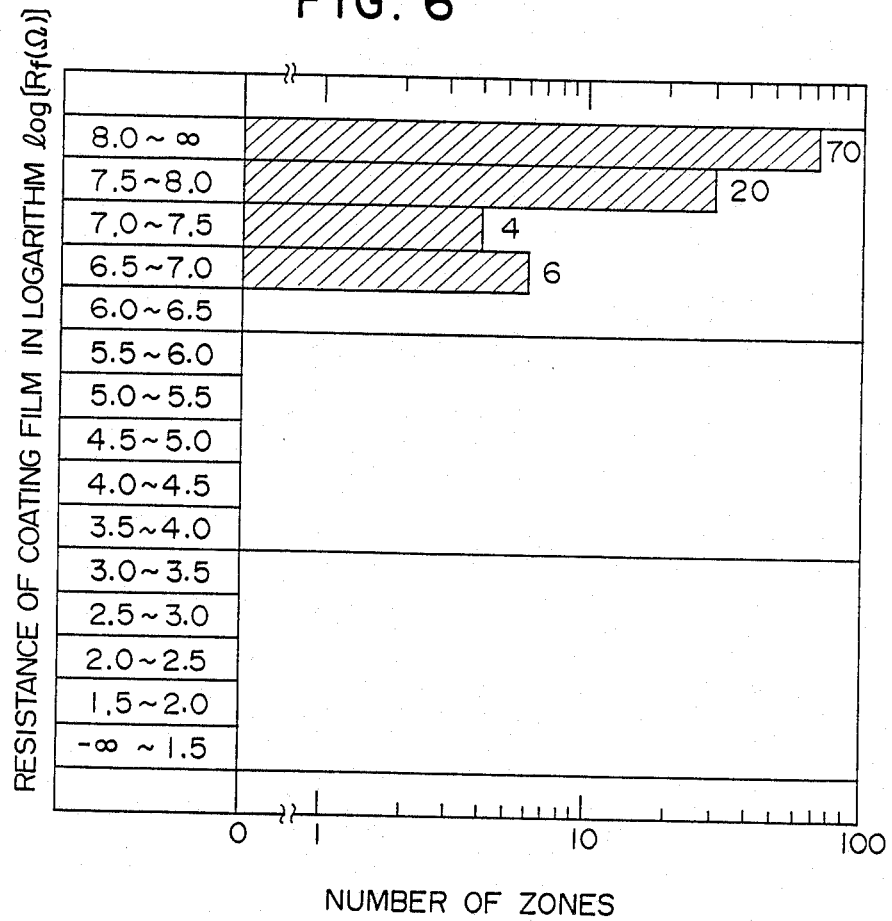
FIGS. 6, 7 and 8 graphically illustrate the results of the measurements performed according to the present invention.

FIG. 6 shows the results of measurement performed for the paint film on the door interior face in a statistical distribution.

The paint film resistance is taken along the ordinate in logarithm with a pitch of 0.5, while the number of zones having the corresponding film resistance values is taken along the abscissa in logarithm to prepare a histogram. It will be seen in FIG. 6 that in the case of the functional paint film, values are concentrated at high resistance regions.

Figure 7:
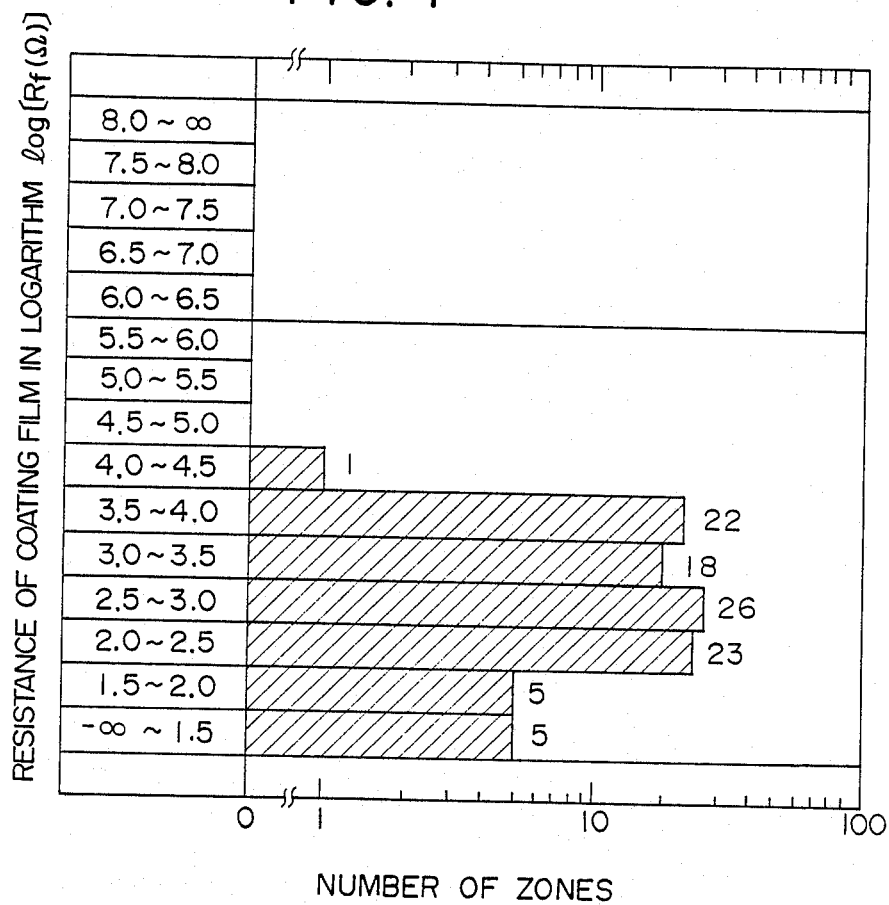

FIG. 7 shows the results of the measurement performed on the portions of the door outer face which underwent significant degradation. When compared with FIG. 6, it will be seen that the values are concentrated at resistance regions where resistance values are much lower.

Figure 8:
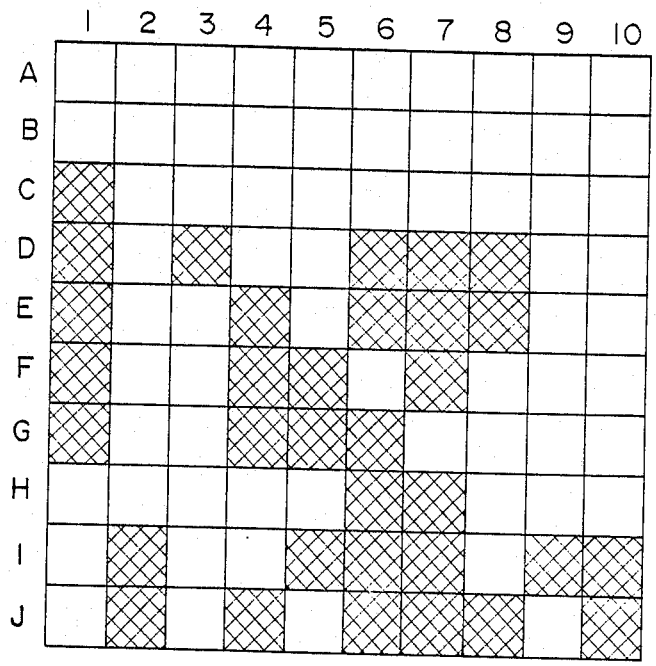

FIG. 8 shows a rearrangement of the data of FIG. 6 in the form of two-dimensional distribution. At the hatched regions, the paint film resistance was not higher than 316 $\Omega$. Careful observation of the portions subjected to the measurement shows, that the regions where the resistance is not higher than 316 $\Omega$ well coincide with those regions where delamination and rust occur. Thus, it can be concluded, that the paint film having the resistance not higher than 316 $\Omega$ has no corrosion protecting capability. Through similar analysis and observation, there are obtained the results shown in table 2 which corresponds to the summarization of the results of the measurement described above and provides the standards for diagnosing degradation of paint films of the oil paint/red lead paint/steel substrate combinations. Thus, according to the invention, it is possible to diagnose quantitatively and nondestructively the degradation of the paint films of oil paint/red lead paint/steel substrate combinations at a high speed.

TABLE 2

| Paint Film Resistance in Logarithm (log[Rf($\Omega$)]) | State | Diagnosis | Rank |
| --- | --- | --- | --- |
| 8.0 ~ $\infty$ | Satisfactory | No aesthetic poblem | A |
| 7.5 ~ 8.0 | | Corrosion protection | |
| 7.0 ~ 7.5 | | is functional | |
| 6.5 ~ 7.0 | | | |
| 6.0 ~ 6.5 | Chalking | No aesthetic poblem | (B$^\sigma$) |
| 5.5 ~ 6.0 | | Corrosion protection | |
| 5.0 ~ 5.5 | | is functional | |
| 4.5 ~ 5.0 | | | B |
| 4.0 ~ 4.5 | | | |
| 3.5 ~ 4.0 | | | |
| 3.0 ~ 3.5 | Exposure of | | (B$^X$) |
| 2.5 ~ 3.0 | ground paint | | |
| 2.0 ~ 2.5 | Film | Corrosion protecting | C |
| 1.5 ~ 2.0 | delamination | capability is | |
| $-\infty$ ~ 1.5 | and rust are observed | lost | |

As will be appreciated from the foregoing description, the degree of degradation of the coating paint films applied to large scale steel buildings and transportation vehicles or tools of which evaluation has heretofore relied upon visual inspection of the outer appearance and the like subjective judgement can now be evaluated and diagnosed quantitatively and accurately according to the teaching of the present invention. Further, the standards for diagnosis has been established for the coating film of oil paint/red lead paint/steel substrate combinations. By preparing the diagnosing standards for other paint/substrate combinations, state of degradation of the coating films of various buildings and transportation facilities can be objectively determined.

Accumulation of data for a variety of paint/substrate combinations through the measurement taught by the invention can ensure the effective utilization as well as extended use life of public and private facilities (determination of the time for recoating and repair and other maintenance factors) and contribute to prevention of failure or accident and economical loss which may be caused by corrosion.

We claim:

1. A method of diagnosing degree of degradation of a coating film on a metal material, comprising the steps of:
   dividing a surface of the coating film on the metal material to be measured into a plurality of small area zones at a predetermined interval;
   measuring impedance indicative of ion transmission resistance of the coating film on the metal material at said zones by an AC impedance measuring method; and
   evaluating degree of degradation of the coating film by statistic distribution of the impedance values of the coating film measured at said zones.

2. A method of diagnosing degree of degradation of a coating film according to claim 1, wherein said impedance measuring step includes substep setting the frequency of a source voltage employed in said AC impedance measuring method at a selected value in dependence on a range of impedance indicative of ion transmission resistance of the coating film to be measured.

3. An apparatus for diagnosing degree of degradation of a coating film on a metal material, comprising:
   a grid-like jig for dividing a surface of the coating film to be measured into a plurality of small area zones of substantially same size;
   a detector having an open mouth portion in close contact with said surface of the coating film at each of said zones, when pushed against said surface, a liquid electrolyte holding chamber communication with said open mouth portion and holding the liquid electrolyte and an electrode for electrolysis disposed within said liquid electrolyte holding chamber; and
   AC impedance measuring means connected to said detector for measuring impedance indicative of ion transmission resistance of the coating film at the zones with which said open mouth portion of said detector is in close contact energizing said detector by an AC source voltage of a controlled frequency.

4. A diagnosis apparatus according to claim 3, further including frequency adjusting means for adjusting the frequency of said source voltage at a selected value depending on a range of the impedance indicative of ion transmission resistance of the coating film to be measured.

5. An apparatus for diagnosing degree of degradation of a coating film on a metal material, comprising:
   a plurality of detectors each having an open mouth portion in close contact with a surface of the coating film on the metal material to be measured when pushed against said surface, a liquid electrolyte holding chamber communicating with said open mouth portion and holding a liquid electrolyte, and an electrode for electrolysis disposed within said liquid electrolyte holding chamber;
   movable detector supporting means for holding said plurality of detectors such that said open mouth portions of said detectors simultaneously pushed against the surface of the coating film in close contact with the surface of said coating film;

a multiplexer having a plurality of input terminal connected to the output terminals of said plural detectors, respectively, and an output terminal connected sequentially to said input terminals; and AC impedance measuring means connected to the output terminal of said multiplexer for measuring impedance indicative of ion transmission resistance of the coating film at the zones with which said open mouth portion of said detector is in close contact, while energizing said detector by an AC source voltage of a controlled frequency.

6. A diagnosis apparatus according to claim 5, further including frequency adjusting means for adjusting the frequency of said source voltage at a selected value depending on a range of the impedance indicative of the ion transmission resistance of the coating film to be measured.

7. A method of diagnosing degree of degradation of a coating film on a metal material, comprising the steps of:

dividing a surface on the coating film of the metal material to be measured into a plurality of small area zones at a predetermined interval;

measuring impedance indicative of ion transmission resistance of the coating film on the metal material at each of said zones by applying an AC source voltage of a selected frequency to the coating film at said zone according to an AC impedance measuring method; and evaluating degree of degradation of the coating film based on two-dimensional pattern in distribution of the impedance values of the coating film measured at said zones, respectively.

8. A method according to claim 7, wherein the frequency of the AC source voltage is set at a selected value depending on a range of the impedance indicative of ion transmission resistance of ion transmission resistance of the coating film resistance to be measured.

* * * * *